United States Patent [19]
Bernstein

[11] Patent Number: 6,096,738
[45] Date of Patent: Aug. 1, 2000

[54] METHOD FOR TREATMENT OF HEADACHE

[75] Inventor: Joel E. Bernstein, Deerfield, Ill.

[73] Assignee: Winston Laboratories, Inc., Vernon Hills, Calif.

[21] Appl. No.: 09/239,198

[22] Filed: Jan. 28, 1999

[51] Int. Cl.[7] .................................................. A61K 31/55
[52] U.S. Cl. .......................... 514/217; 514/450; 514/643; 514/649
[58] Field of Search .................................. 514/217, 450, 514/643, 649

[56] References Cited

U.S. PATENT DOCUMENTS 4,395,420  7/1983  Bernstein .
4,603,131  7/1986  Bernstein et al. .

OTHER PUBLICATIONS

Medline AN 1998092654, Richeimer et al. Clin J Pain 13(4) Abstract, Dec. 1997.

Embase AN 89121253, Ranga et al, Am Fam. Phys. 39(4) Abstract, 1989.

*Primary Examiner*—Rebecca Cook
*Attorney, Agent, or Firm*—Jones, Day, Reavis & Pogue

[57] ABSTRACT

A method for preventing and treating headache pain comprising administering a tricyclic antidepressant compound locally to the nasal mucosa to a patient suffering from headaches.

8 Claims, No Drawings

METHOD FOR TREATMENT OF HEADACHE

BACKGROUND OF THE INVENTION

Headache pain affects millions of people in the United States each year. While there are a wide assortment of products used to treat headache, ranging from simple analgesics like aspirin and acetaminophen to opiate analgesics such as butorphanol, none of these treatment modalties are invariably effective. All have potentially serious side effects which can greatly limit their usefulness in many subgroups of patients. Consequently, it is desirable to have new alternative headache remedies available in the marketplace.

I have discovered that tricyclic antidepressants usually prescribed orally for relief of mental depression, applied topically to the skin to relieve itching in dermatitis (as described in my prior U.S. Pat. No. 4,395,420, incorporated herein by reference), or applied topically to the mucous membranes of the nose to prevent or treat irritation of the mucous membranes of the nose (as described in my prior U.S. Pat. No. 4,603,131, incorporated herein by reference), are surprisingly effective at preventing the occurrence of headache pain or relieving the pain in subjects experiencing headache pain when applied topically to the nasal mucosa. These compounds include the pharmaceutically acceptable salts of the tricyclics. The term pharmaceutically acceptable salts, as used herein, refers to the physiologically acceptable acid addition salts such as hydrochloride, hydrobromide, hydroiodide, acetate, valerate, oleate, etc. Doxepin, amitriptyline and imipramine respectively are the tertiary amine derivatives of dibenzoxepin, dibenzocycloheptadiene and dibenzazepine wherein the nitrogen atom is connected to the ring structure by a three carbon aliphatic chain and the tertiary amine has two carbon atoms attached thereto in addition to the aliphatic chain.

The present invention relates to a method for topically treating headache pain. The principal object of the present invention is to apply to the nasal mucosa doses of tricyclic antidepressant compounds traditionally employed systemically for the treatment of mental depression to prevent or relieve headache pain.

This and other objects of the present invention may be more readily understood when considered in conjunction with the following detailed description and examples.

DETAILED DESCRIPTION OF THE PREFERRED EMBODIMENTS

I investigated the possible therapeutic effects of topically applying to the nasal mucosa formulations of tricyclic antidepressant in order to prevent or relieve headache pain. Patients who commonly suffer from headache pain noted fewer and less severe headaches when utilizing formulations of tricyclic antidepressants applied to their nasal mucosa. In the practice of the invention, concentrations of doxepin, amitriptyline, imipramine and other tricyclic antidepressants and their salts varying from 0.01% by weight to about 1% by weight will be incorporated into vehicles suitable for application to the nasal mucosa and administered to patients suffering from headache pain. Suitable vehicles for applications include nasal gels, nasal creams, and nasal solutions, each of which are applied directly to the nasal mucosa. Nasal solutions can be applied either as a spray, or as drops as disclosed in the aforementioned U.S. Pat. No. 4,603,131. The preferred amount of active ingredients will be from about 0.05% to about 1.0% by weight of the carrier.

The following examples further illustrate the invention. In these examples, all percentages are by weight of the carrier.

EXAMPLE 1

Thirty-four (34) normal subjects received a nasal spray, containing a solution of 0.8% doxepin hydrochloride over a four-week period administered once daily as a metered spray of 50 microliters per nostril in each nostril. Thirty-two of these patients experienced no headaches whatsoever over the four week period.

EXAMPLE 2

Fifteen (15) patients with a history of seasonal allergic rhinitis received during the allergy season a nasal spray containing a solution of 0.4% doxepin hydrochloride twice daily for fourteen consecutive days, administered as a metered spray of 50 microliters per nostril in each nostril. No patient experienced even a single headache during this closing period.

EXAMPLE 3

One hundred eighty (180) patients with a history of seasonal allergic rhinitis received during the allergy season a nasal spray containing either a solution of 0.2% doxepin hydrochloride (60 patients), a solution of 0.4% doxepin hydrochloride (60 patients) or the vehicle solution without doxepin (60 patients), twice daily for fourteen consecutive days, administered as a metered spray of 50 microliters per nostril in each nostril. The 120 patients administering doxepin to their nasal mucosa had a total of 16 headache episodes over the two-week treatment period versus 14 headache episodes in the 60 patients receiving vehicle solution. This translates into a mean headache incidence of 0.23 in vehicle-treated patients verus 0.13 in doxepin-treated patients.

EXAMPLE 4

Thirty (30) patients with a history of seasonal allergic rhinitis and receiving an allergenic substance were treated with a nasal spray containing doxepin hydrochloride 0.05% for one day, administered as a metered spray of 50 microliters per nostril in each nostril. None of the patients reported a headache episode during the treatment period.

What is claimed is:

1. A method for the treatment of headache pain in a human, comprising topically administering to the nasal mucosa of said human a composition comprising about 0.01%–1.0% by weight of a tricyclic antidepressant compound in a pharmaceutically acceptable vehicle.

2. The method of claim 1 wherein said tricyclic antidepressant compound is selected from the group consisting of doxepin, amitriptyline and imipramine or a physiologically acceptable acid addition salt thereof.

3. The method of claim 2 wherein said physiologically acceptable acid addition salt is selected from the group consisting of the hydrochloride, hydrobromide, hydroiodide, acetate, valerate and oleate.

4. The method of claim 1 wherein said pharmaceutically acceptable vehicle is selected from the group consisting of a nasal spray, nasal drops, a nasal solution, a nasal gel, and a nasal cream.

5. A method for preventing headache pain in a human, comprising topically administering to the nasal mucosa of said human a composition comprising about 0.01%–1.0% by weight of a tricyclic antidepressant compound in a pharmaceutically acceptable vehicle.

6. The method of claim 5 wherein said tricyclic antidepressant compound is selected from the group consisting of doxepin, amitriptyline and imipramine or a physiologically acceptable acid addition salt thereof.

7. The method of claim 5 wherein said physiologically acceptable acid addition salt is selected from the group consisting of the hydrochloride, hydrobromide, hydroiodide, acetate, valerate and oleate.

8. The method of claim 5 wherein said pharmaceutically acceptable vehicle is selected from the group consisting of a nasal spray, nasal drops, a nasal solution, a nasal gel, and a nasal cream.

* * * * *